US00PP24433P2

(12) United States Plant Patent
Kanaya

(10) Patent No.: US PP24,433 P2
(45) Date of Patent: May 6, 2014

(54) ***CALIBRACHOA* PLANT NAMED 'SUNCALWINE'**

(50) Latin Name: ***Calibrachoa* sp.**
Varietal Denomination: Suncalwine

(75) Inventor: Takeshi Kanaya, Chiba (JP)

(73) Assignee: Suntory Flowers Limited, Tokyo (JP)

( * ) Notice: Subject to any disclaimer, the term of this patent is extended or adjusted under 35 U.S.C. 154(b) by 137 days.

(21) Appl. No.: 13/506,498

(22) Filed: Apr. 23, 2012

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — June Hwu
(74) *Attorney, Agent, or Firm* — C. A. Whealy

(57) ABSTRACT

A new and distinct cultivar of *Calibrachoa* plant named 'Suncalwine', characterized by its compact, upright, outwardly spreading and mounding plant habit; vigorous growth habit; freely branching and flowering plant habit; early and long flowering period; numerous single purple-colored flowers with darker purple-colored venation; and good garden performance.

1 Drawing Sheet

Botanical designation: *Calibrachoa* sp.
Cultivar denomination: 'SUNCALWINE'.

BACKGROUND OF THE INVENTION

The present invention relates to a new and distinct cultivar of *Calibrachoa* plant, botanically known as *Calibrachoa* sp. and hereinafter referred to by the name 'Suncalwine'.

The new *Calibrachoa* plant is a product of a planned breeding program conducted by the Inventor in Higashiomi, Shiga, Japan. The objective of the breeding program is to develop new compact, mounding and freely branching *Calibrachoa* plants with attractive and uniquely colored flowers.

The new *Calibrachoa* plant is a naturally-occurring branch mutation of a proprietary selection of *Calibrachoa* sp. identified as code number 2572-2, not patented. The new *Calibrachoa* plant was discovered and selected by the Inventor on a single flowering plant within a population of plants of the mutation parent selection in a controlled greenhouse environment in Higashiomi, Shiga, Japan in September, 2008.

Asexual reproduction of the new *Calibrachoa* plant by vegetative cuttings in a controlled greenhouse environment in Higashiomi, Shiga, Japan since September, 2008 has shown that the unique features of this new *Calibrachoa* plant are stable and reproduced true to type in successive generations.

SUMMARY OF THE INVENTION

Plants of the new *Calibrachoa* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Suncalwine'. These characteristics in combination distinguish 'Suncalwine' as a new and distinct *Calibrachoa* plant:

1. Compact, upright, outwardly spreading and mounding plant habit.
2. Vigorous growth habit.

3. Freely branching and flowering plant habit.
4. Early and long flowering period.
5. Numerous single purple-colored flowers with darker purple-colored venation.
6. Good garden performance.

Plants of the new *Calibrachoa* can be compared to plants of the mutation parent selection. Plants of the new *Calibrachoa* differ primarily from plants of the mutation parent selection primarily in flower color as plants of the mutation parent selection have red purple-colored flowers.

Plants of the new *Calibrachoa* can also be compared to plants of *Calibrachoa* 'Sunbelao', disclosed in U.S. Plant Pat. No. 22,391. In side-by-side comparisons conducted in Higashiomi, Shiga, Japan, plants of the new *Calibrachoa* and 'Sunbelao' differed primarily in the following characteristics:

1. Plants of the new *Calibrachoa* had smaller leaves than plants of 'Sunbelao'.
2. Plants of the new *Calibrachoa* had smaller flowers than plants of 'Sunbelao'.
3. Plants of the new *Calibrachoa* and 'Sunbelao' differ in petal lobe shape.
4. Plants of the new *Calibrachoa* and 'Sunbelao' differed in flower color as plants of 'Sunbelao' had purple violet-colored flowers with dark purple-colored venation.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the top of the sheet comprises a side perspective view of a typical flowering plant of 'Suncalwine' grown in a container.

The photograph at the bottom of the sheet is a close-up view of a typical flowering plant of 'Suncalwine'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Calibrachoa* production. During the production of the plants, day temperatures averaged 23° C. and night temperatures averaged 13° C. Plants were four months old when the photographs and the description were taken. In the following description, color references are made to The Royal Horticultural Society Colour Chart, 2007 Edition, except where general terms of ordinary dictionary significance are used.

Botanical classification: *Calibrachoa* sp. 'Suncalwine'.

Parentage: Naturally-occurring branch mutation of a proprietary selection of *Calibrachoa* sp. identified as code number 2572-2, not patented.

Propagation:

*Type.*—By vegetative cuttings.

*Time to initiate roots, summer.*—About one week at 15° C. to 20° C.

*Time to produce a rooted young plant, summer.*—About three weeks at 15° C. to 20° C.

*Root description.*—Fibrous; white in color.

*Rooting habit.*—Freely branching.

Plant description:

*Plant and growth habit.*—Compact, upright, outwardly spreading and mounding plant habit; freely branching habit with numerous lateral branches developing per plant; pinching enhances lateral branch development; vigorous growth habit.

*Plant height.*—About 18.6 cm.

*Plant diameter.*—About 53.2 cm.

Lateral branch description:

*Length.*—About 25.3 cm.

*Diameter.*—About 1.4 mm.

*Internode length.*—About 1.6 cm.

*Strength.*—Strong.

*Aspect.*—Upright to outwardly.

*Texture.*—Pubescent.

*Color.*—Close to 144B.

Foliage description:

*Arrangement.*—Alternate, simple.

*Length.*—About 3.2 cm.

*Width.*—About 1.1 cm.

*Shape.*—Narrowly elliptic.

*Apex.*—Obtuse.

*Base.*—Cuneate.

*Margin.*—Entire.

*Texture, upper and lower surfaces.*—Pubescent.

*Venation pattern.*—Pinnate; reticulate.

*Color.*—Developing leaves, upper surface: Close to 137D. Developing leaves, lower surface: Close to 138B. Fully expanded leaves, upper surface: Close to N138B; venation, close to 144B. Fully expanded leaves, lower surface: Close to N138C; venation, close to 138B.

*Petiole.*—Length: About 3.5 mm. Diameter: About 0.5 mm. Texture, upper and lower surfaces: Pubescent. Color, upper and lower surfaces: Close to 143B.

Flower description:

*Flower arrangement and habit.*—Single salverform flowers arising from upper leaf axils; freely flowering habit with usually about 80 flowers developing per plant; flowers face upright or outwardly.

*Fragrance.*—None detected.

*Natural flowering season.*—Early flowering habit, plants of the new *Calibrachoa* initiate and develop flowers about three to four weeks after planting; long flowering period, flowering commences naturally during the spring and plants flower continuously throughout the summer until late autumn in Japan.

*Flower longevity.*—Individual flowers last about seven to ten days on the plant; flowers not persistent.

*Flower diameter.*—About 3.2 cm.

*Flower length (depth).*—About 2.7 cm.

*Throat diameter.*—About 7.4 mm.

*Tube length.*—About 1.8 cm.

*Tube diameter, base.*—About 3.1 mm.

*Flower bud.*—Shape: Cylindrical. Length: About 2.5 cm. Diameter: About 1.1 cm. Color: Towards the apex, close to 72B; mid-section, close to 4B; towards the base, close to 150A.

*Corolla.*—Arrangement: Five petals fused at the base and opening into a flared trumpet. Petal length from throat: About 1.3 cm. Petal width: About 1.4 cm. Petal shape: Spatulate. Petal apex: Rounded. Petal margin: Entire. Petal texture, upper and lower surfaces: Smooth, glabrous. Throat texture: Smooth, glabrous. Tube texture: Pubescent. Color: Petal, when opening, upper surface: Close to N78A. Petal, when opening, lower surface: Close to N78D. Petal, fully opened, upper surface: Close to N78A; color becoming closer to N78C with development; venation, close to N79C. Petal, fully opened, lower surface: Close to N80D; venation, close to N80B. Throat: Close to 7B; venation, close to N78A. Tube: Close to 8B; venation, close to N80B.

*Calyx.*—Arrangement: One star-shaped calyx tube with five sepals fused at the base. Sepal length: About 7 mm to 11 mm. Sepal width: About 2.4 mm. Sepal shape: Lanceolate. Sepal apex: Acute. Sepal margin: Entire. Sepal texture, upper and lower surfaces: Pubescent. Sepal color: Immature, upper surface: Close to 143B. Immature, lower surface: Close to 143C. Mature, upper surface: Close to 143A. Mature, lower surface: Close to 143B.

*Peduncles.*—Length: About 1.5 cm. Diameter: About 0.6 mm. Angle: Upright to outwardly. Strength: Strong. Texture: Pubescent. Color: Close to 143C.

*Reproductive organs.*—Stamens: Quantity: Five per flower. Stamen length: About 8 mm to 10 mm. Anther shape: Ellipsoidal. Anther size: About 0.9 mm by 1.3 mm. Anther color: Close to 1C. Pollen amount: Scarce. Pollen color: Close to 5A. Pistils: Quantity: One per flower. Pistil length: About 10.6 mm. Style color: Close to 145C. Stigma shape: Transversely ellipsoidal. Stigma color: Close to 144C. Ovary color: Close to 144B.

*Seeds and fruits.*—Seed and fruit development have not been observed on plants of the new *Calibrachoa*.

Garden performance: Plants of the new *Calibrachoa* have been observed to have good garden performance and to tolerate wind, rain and temperatures ranging from about −5° C. to about 35° C.

Pathogen & pest resistance: Plants of the new *Calibrachoa* have not been observed to be resistant to pests and pathogens common to *Calibrachoa* plants.

It is claimed:

1. A new and distinct *Calibrachoa* plant named 'Suncalwine' as illustrated and described.

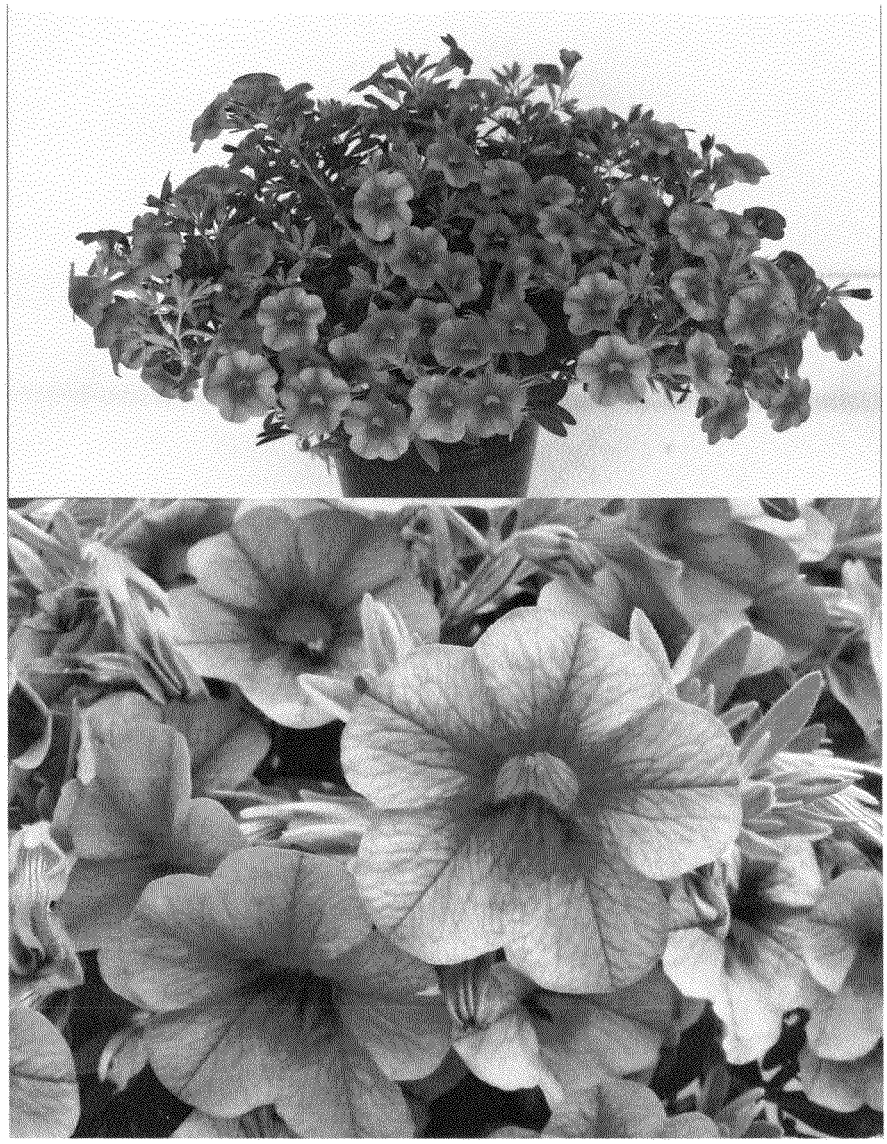

* * * * *